United States Patent [19]

Winters

[11] Patent Number: 5,059,206
[45] Date of Patent: Oct. 22, 1991

[54] METHOD AND APPARATUS FOR REPAIRING A TEAR IN A KNEE MENISCUS

[76] Inventor: Thomas F. Winters, 1711 Venetian Way, Winter Park, Fla. 32789

[21] Appl. No.: 336,803

[22] Filed: Apr. 12, 1989

[51] Int. Cl.⁵ .............................................. A61B 17/04
[52] U.S. Cl. ................................... 606/213; 606/220; 606/77
[58] Field of Search .................... 227/19; 606/60, 65, 606/66, 67, 72, 73, 74, 77, 87, 88, 104, 139, 142, 143, 213, 220

[56] References Cited

U.S. PATENT DOCUMENTS

| | | | |
|---|---|---|---|
| 4,653,486 | 3/1987 | Coker | 606/65 |
| 4,796,612 | 1/1989 | Reese | 606/72 |
| 4,884,572 | 12/1989 | Bays et al. | 411/510 X |
| 4,895,148 | 1/1990 | Bays et al. | 606/213 |

Primary Examiner—Robert A. Hafer
Assistant Examiner—Kerry Owens
Attorney, Agent, or Firm—Duckworth, Allen, Dyer & Doppelt

[57] ABSTRACT

A method and apparatus for repairing a tear in a knee meniscus of a patient utilizes a delivery device having a distal end dimensioned to extend into the interior of the patient's knee. A fastener is fitted within the distal end and is manipulated to extend toward the tear in the meniscus, and extended across the tear to close and bind the tear without passing out of the knee.

11 Claims, 5 Drawing Sheets

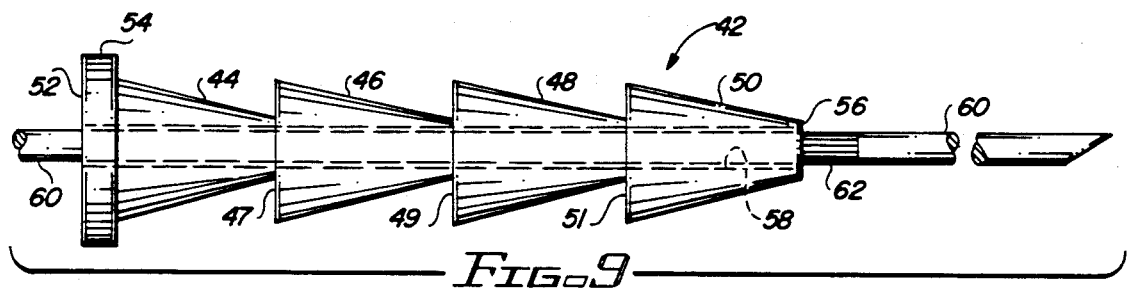
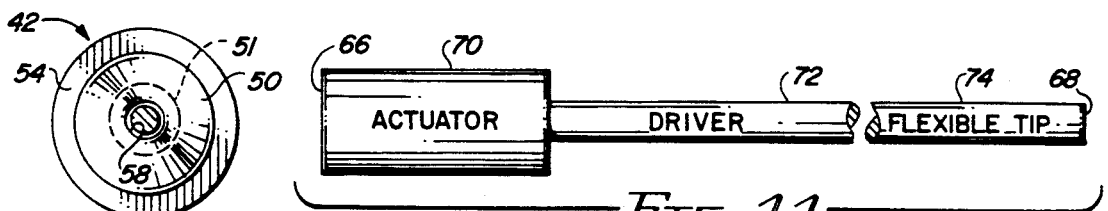
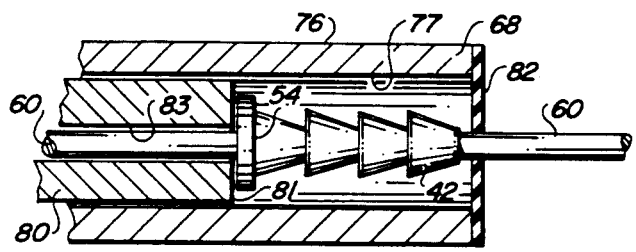
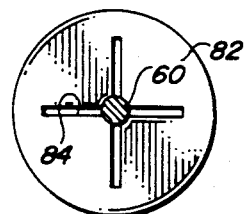
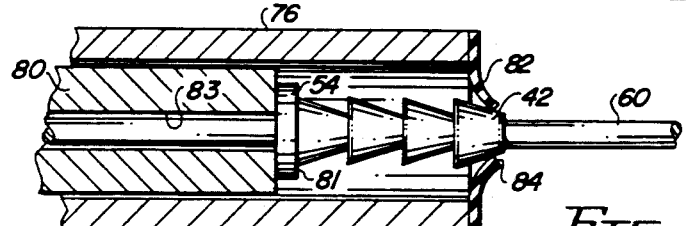
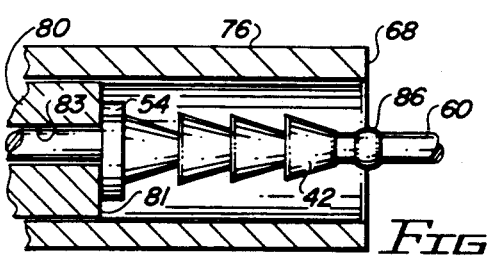
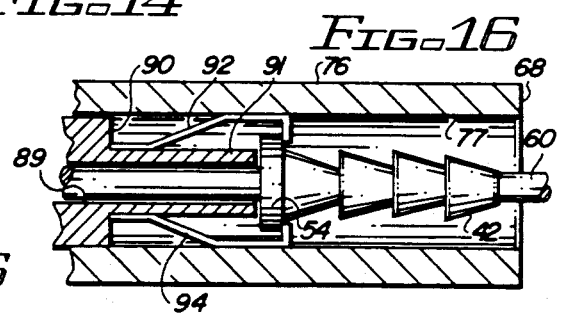
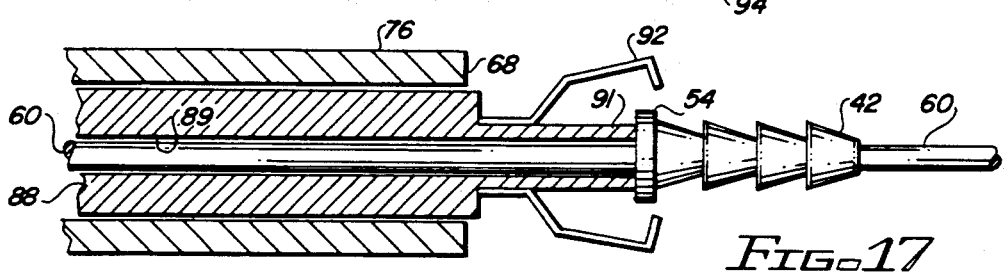

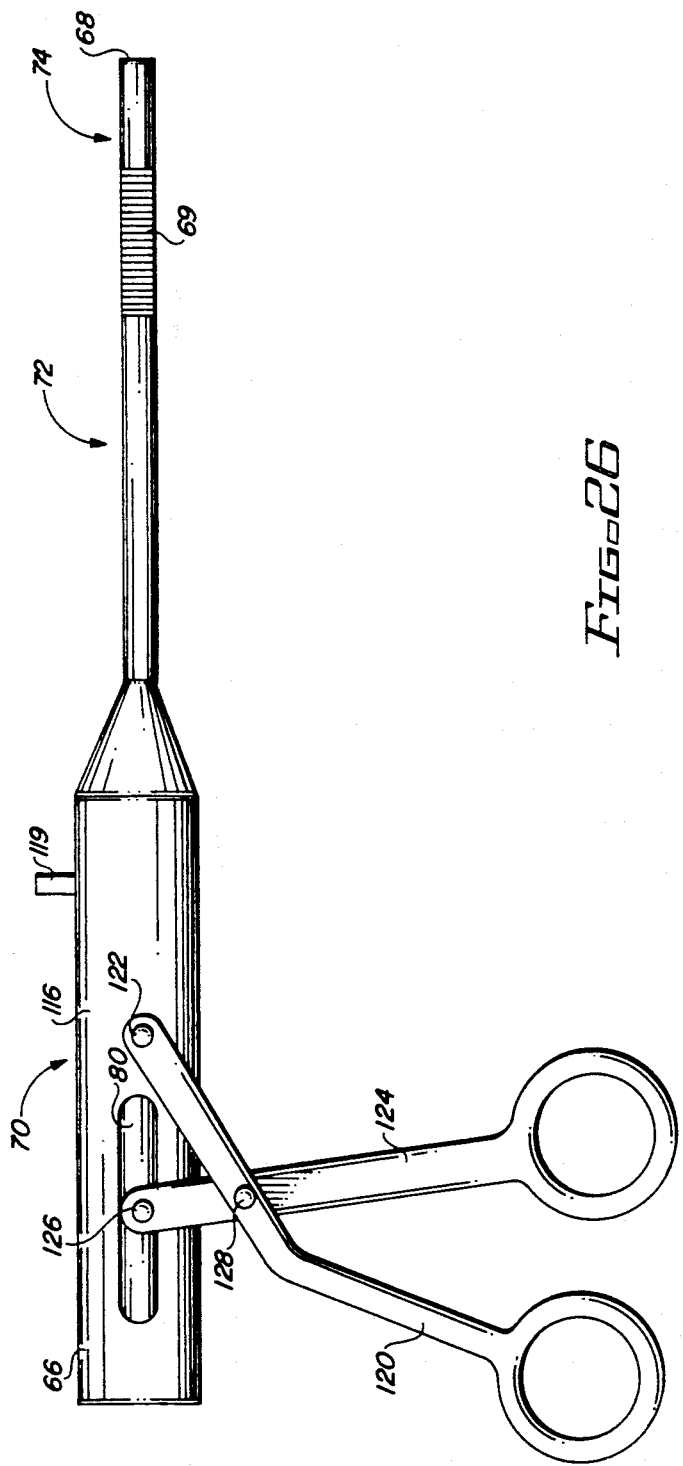
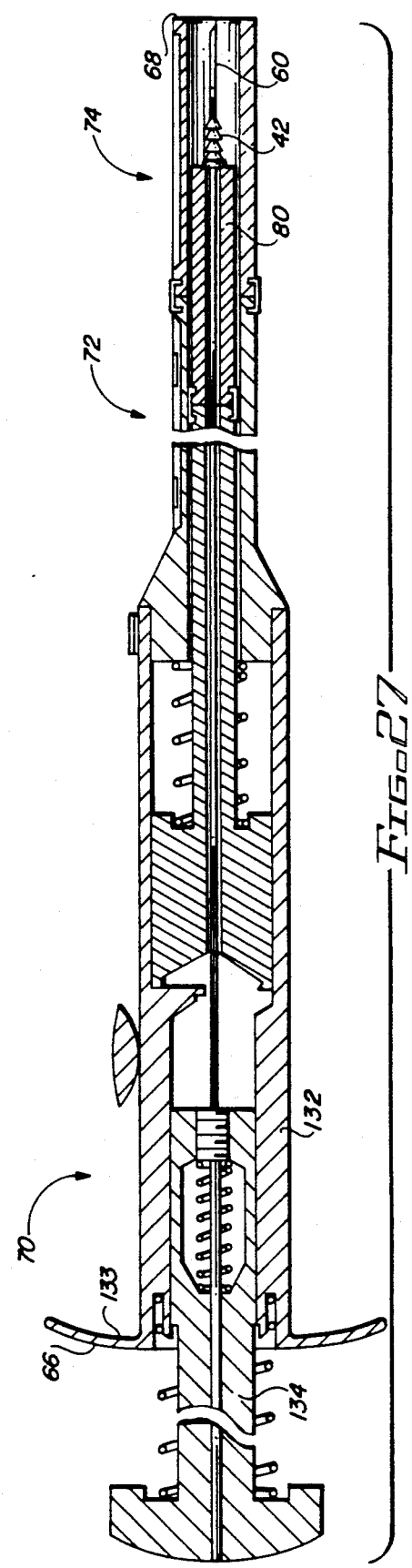

METHOD AND APPARATUS FOR REPAIRING A TEAR IN A KNEE MENISCUS

BACKGROUND OF THE INVENTION

1. Field of the Invention

The present invention relates generally to the orthopedic surgical arts, and more specifically to methods and apparatus for repairing a tear in a knee meniscus.

2. Description of the Prior Art

The term "meniscus" describes a fibrous cartilage located within human joints which functions to absorb shock and prevent friction during joint movement. There are two generally crescent-shaped meniscus on opposite sides of the human knee. Frequently, a tear develops in one of the knee meniscus, causing pain and discomfort. Unless treated, a torn knee meniscus may frequently deteriorate, causing additional complications.

In treating a torn knee meniscus, open meniscectomy was previously a common orthopedic procedure. In 1948, the degenerative characteristics of a total meniscectomy were reported; nevertheless, the use of total meniscectomy continued for many years, for want of a better procedure. See Fairbank, "Knee Joint Changes After Meniscectomy", *Journal of Bone and Joint Surgery*, 30-B (4): pp. 664–670 (1948). Partial meniscectomy proved to be effective; however, there was continued evidence that the destructive changes noted by Fairbank may also accompany a partial meniscectomy.

Recently, researchers have begun directing efforts at meniscal preservation via primary surgical repair, using arthroscopy. Scott et al, "Combined Posterior Incision and Arthroscopic Intra-articular Repair"; *Journal of Bone and Joint Surgery*, 68-A: pp. 847–861 (1986). The surgical repair technique requires the passage of sutures and surgical needles through the knee capsule, which are tied externally. See Scott et al, supra, and DeHaven, "Peripheral Meniscus Repair: An Alternative to Meniscectomy", *Orthop. Trans.* 5:399–400 (1981). There are a number of drawbacks to this procedure, including the need for an accessory incision in the back of the knee, potential injury to the nerves and blood vessels by passing the needle through the knee, as well as the additional time and advanced skills required.

There are a number of stapling instruments disclosed in the prior art which are useful for orthopedic purposes. For example, in U.S. Pat. No. 4,580,563, Gross discloses an arthroscopic stapling instrument for repairing capsular disruptions associated with shoulder dislocations and subluxations.

SUMMARY OF THE INVENTION

The present invention is directed to a method and apparatus for repairing a tear in a knee meniscus of a patient. In accordance with the method and apparatus, a delivery device is provided having proximal end, and also a distal end which is dimensioned to extend into the interior of the patient's knee. A fastener, such as a staple, is fitted within the delivery device and the distal end of the device is manipulated so that the distal end is directly outwardly toward the tear in the meniscus. The fastener is then extended and released from the distal end outwardly through the meniscus and across the tear to close and bind the tear without passing out of the knee. Preferably, the device is fitted with a needle at the distal end, so that the needle may first be extended across the meniscal tear to provide a channel for delivery of the fastener. The fastener is extended out of the distal end by pushing the fastener through the device responsive to an actuating step conducted at the proximal end. Suitably, the fastener is both nontoxic and bioabsorbable, and is further constructed and positioned in the meniscus so as to avoid condylar abrasion.

The fastener is provided with locking means, such as protrusions or barbs, along the periphery of its length in order to lock the fastener across the tear and prevent movement.

In accordance with another aspect of the present invention, the apparatus is provided with means for driving the fastener through the distal end of the device, while the distal end is turned or flexed, in order to direct the distal end toward the meniscal tear under repair.

DESCRIPTION OF THE DRAWING

FIGS. 9 and 10 are side and front elevations, respectively, of another fastener for repairing meniscal tears in accordance with the present invention.

FIG. 11 is a schematic illustration of a fastener delivery system in accordance with the present invention.

FIG. 12 is a cross-sectional side view of the distal portion of one embodiment of a fastener delivery system in accordance with the present invention, and FIG. 13 is a front view of the portion shown in FIG. 12.

FIG. 14 is a cross-sectional side view like FIG. 12, illustrating the operation of the fastener delivery system.

FIG. 15 is a cross-sectional side view of an alternate embodiment of the distal portion of the delivery system.

FIGS. 16 and 17 are cross-sectional side views illustrating the operation of another embodiment of the distal portion of the fastener delivery system.

FIG. 26 illustrates the overall construction of one embodiment of the fastener delivery system.

FIG. 27 illustrates the overall construction of another embodiment of the fastener delivery system.

DETAILED DESCRIPTION

Figure 1:
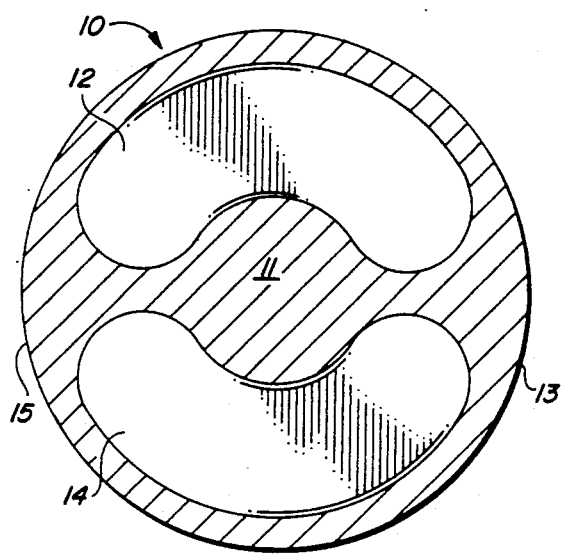
FIG. 1 is a simplified cross section of the human knee, illustrating the menisci.

As is shown in FIG. 1, the human knee (shown schematically in cross-section and referred to generally by the reference numeral 10) contains two opposing, crescent-shaped menisci 12, 14. The knee 10 is defined by a central, interior portion 11 and anterior and posterior peripheries, 13 and 15, respectively.

Figure 3:
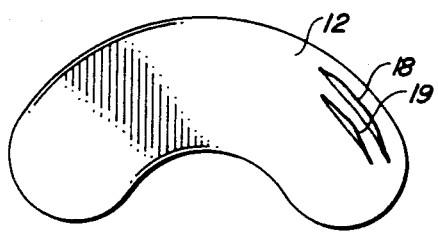
FIGS. 2–5 illustrate typical tear patterns in the human knee meniscus.
Figure 4:
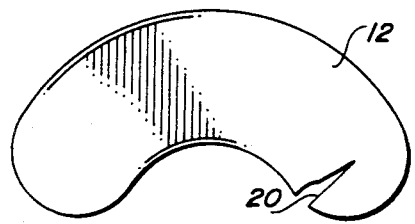
Figure 2:
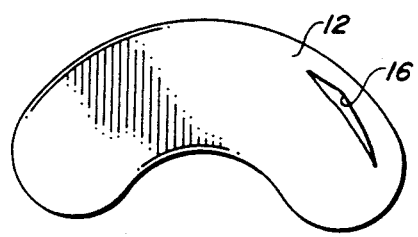
Figure 5:
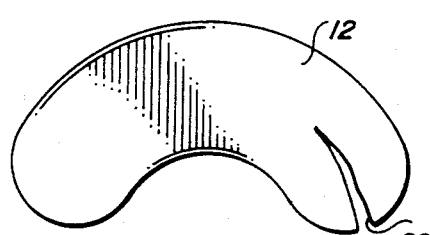

As is noted above, the present invention is directed to the repair of tears that are frequently experienced in the knee menisci. Typical types of tears in the knee menisci are shown in FIGS. 2–5. In FIG. 2, the tear 16 is generally described as a single longitudinal tear, and represents a majority of the meniscal tears that are experienced. In FIG. 3, there are two tears 18, 19 which are generally referred to as a "double longitudinal" tear. In FIG. 4, the tear 20 is referred to as a radial tear, and in FIG. 5 the tear 22 is generally described as a "flap". There are also other types of tears, but the tears shown in FIGS. 2-5 represent the large majority of tears that are experienced.

The manner in which meniscal tears are to be repaired in accordance with the method and apparatus of the present invention will now be described with reference to FIGS. 6-27.

Figure 6:
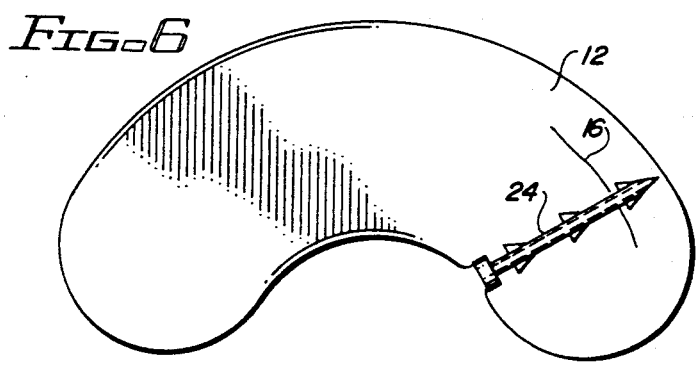
FIG. 6 illustrates the use of the method and apparatus of the present invention for repairing a tear in a human knee meniscus.

Noting FIG. 6, the meniscus 12 is shown with a single longitudinal tear 16. In order to permit the tear to mend, a fastener 24 is injected outwardly and generally radially from the center of the knee through the meniscus 12 and thence through both sides of the tear 16, causing the two sides of the tear to come together and close. It will be noted that the fastener is extended into the meniscus 12 in a manner which avoids damage to the nerves and blood vessels posterior to the meniscus. Preferably, the fastener 24 is positioned such that at least one barb 36, described in detail below, is outwardly from the tear 16.

Figure 8:
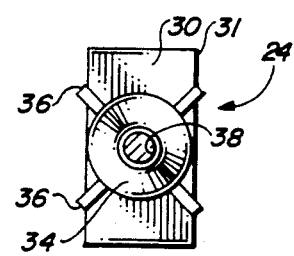
FIGS. 7 and 8 are side and front views, respectively, of a fastener for repairing meniscal tears in accordance with the present invention.
Figure 7:
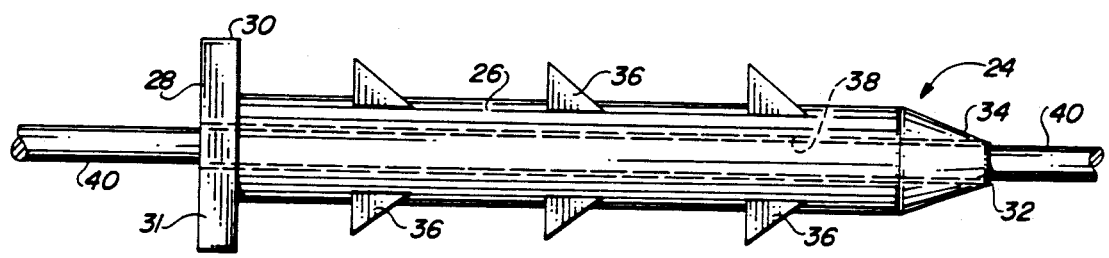

Two embodiments of a fastener suitable for repairing tears in a knee meniscus in accordance with the present invention are shown in FIGS. 7-9.

Noting the embodiment of FIGS. 7 and 8, the fastener 24 comprises a cylindrical member 26 of a non-toxic, bioabsorbable material such as D,L'polyglycolic acid. These types of materials have a known safety record, and are capable of being fabricated into fasteners like that shown in FIGS. 7 and 8.

The tubular member 26 includes a flat proximal end 28 and a forward distal end 32 defined by a tapered surface 34. The member 26 includes a central lumen 38 dimensioned to receive a guide wire or needle 40. The proximal end 28 may include a head member 30 which has two flat surfaces 31, the dimension between which surfaces is generally the same as the diameter of the member 26 (note FIG. 8). As will be described in greater detail below, the construction of the head member 30 and the manner in which the fastener 24 is oriented and inserted into the meniscus 12 is chosen to avoid condylar abrasion during the recovery period, and before complete absorption of the fastener 24 into the recipient meniscus.

As is further shown in FIGS. 7 and 8, the fastener 24 includes a plurality of locking barbs 36 along the outer periphery of the tubular member 26. Upon insertion, the locking barbs 36 lock the fastener in place and prevent movement of the fastener 24.

A second embodiment of a fastener in accordance with the present invention will now be described with reference to FIGS. 9 and 10, in which the fastener 42 is fabricated from a series of truncated cones 44, 46, 48 and 50 which are integrally molded together so that the tapered surface of each cone extends toward the distal end 56 of the fastener 42. The fastener 42 further includes a flat proximal end 52 and may include a head member 54, as well as a central lumen 58 adapted to receive a delivery device 60 (i.e., a guide wire or needle) therein. As thus defined, the fastener 42 includes plural locking surfaces 47, 49 and 51 along the back surface of three of the truncated cones, which serve to lock the fastener 42 against movement after insertion through a meniscus and across a tear. The delivery device 60 includes striations or knurling 62 for frictionally holding the fastener 42 in place, until pressure against the proximal surface 52 overcomes that friction, and drives the fastener across the distal extremity of the delivery device, as is more particularly described below.

Systems and methods for delivering a meniscal fastener into the central portion of the knee and thence outwardly through the meniscus to repair a tear are described with reference to FIGS. 11-27.

FIG. 11 illustrates the portions of a fastener delivery system schematically, and is referred to generally by the reference numeral 64. The delivery system includes a proximal end 66 and a distal end 68, the distal end being dimensioned to extend into the central portion of the knee. The system 64 further includes a flexible tip 74 at the distal end, which may be oriented in the desired direction of the tear under treatment after insertion into the knee's central portion. A fastener (such as either fastener 24 or 42 of FIGS. 7 and 9) is positioned in the flexible tip portion 74, and is driven out of the distal end 68 via action along a driver section 72 of the system 64, which in turn is operated by an actuator 70 outside the patient's knee at the proximal end 66.

Alternate constructions of the flexible tip portion 74 of the delivery system 64 are shown and described with reference to FIGS. 12-17.

Noting first FIGS. 12-14, the flexible tip portion includes the end of a cylindrical delivery device 76 having a lumen 77 through which a pushing driver mechanism 80 extends. The driver 80 in turn has a central lumen 83 through which the guide wire or needle 60 extends, with the driver terminating at a forward extremity 81 which abuts the proximal end of the fastener 42 and which, in operation, pushes against the head 54. A membrane 82 is fixed at the distal end 68, the membrane including plural slots 84 so as to permit the guide wire or needle 60 to be pushed out of the delivery device 76, and thereafter permit the fastener 42 to be pushed out of the delivery device, along the guide wire or needle 60 and thence through the meniscus under treatment, as is shown in FIG. 14.

FIG. 15 shows an alternate construction, in which the membrane 82 is omitted from the distal end 68. In lieu of the striations 62 shown in FIG. 9, a peened area 86 is formed on the guide wire or needle 60, to frictionally engage the fastener 42 until that friction is overcome by operation of the drive 80 to push the fastener 42 along the guidewire or needle.

A third form of construction for the flexible tip portion 74 of the system 64 (FIG. 11) is shown in FIGS. 16 and 17. This arrangement is similar to the arrangement of FIGS. 12-15, except that the driver 88 includes a cut-away portion 90 forming a reduced diameter tube 91 within the delivery device 76. A pair of engaging jaws 92, 94 are fitted within the reduced diameter area, and engage the head 54 of the fastener 42 and are biased by the inside diameter of the lumen 77, until the driver 88 extends the reduced diameter portion 91 out of the distal end 68, as is shown in FIG. 17. At that time, the opposing jaws 92, 94 open outwardly, and permit the fastener to remain locked in place within the meniscus after insertion.

Construction details of the driver section 72 of the fastener delivery system 64 (FIG. 11) will now be described with reference to FIGS. 18-22.

Figure 18:
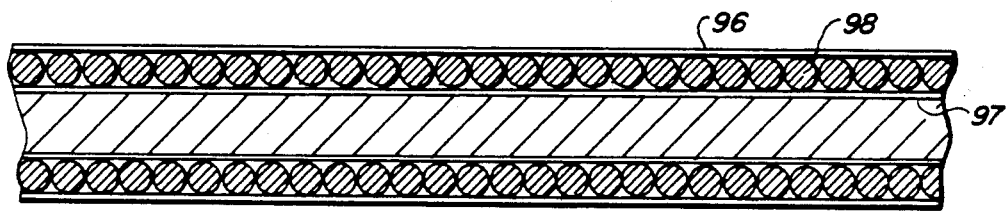
FIGS. 18–22 illustrate various alternative construction details for the intermediate portion of the fastener delivery system.
Figure 19:
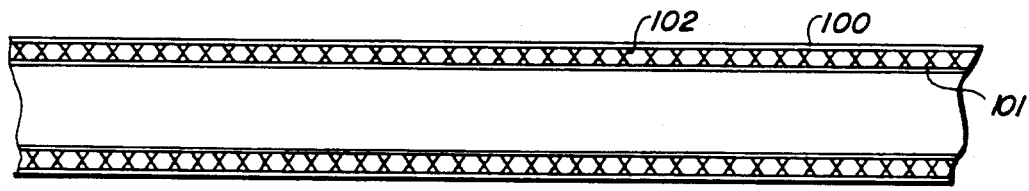

FIGS. 18 and 19 show alternate construction arrangements for the wall of the delivery device 72, in order to achieve a degree of flexibility. For example, in FIG. 18 the delivery device 96 has a central lumen 97 and a continuous length of wire 98 helically wound around the outer wall in a conventional manner, so as to achieve the desired flexibility. In the embodiment of FIG. 19, the delivery device 100 has a central lumen 101 and braided wire 102 along its walls, in order to achieve the desired flexibility.

Figure 20:
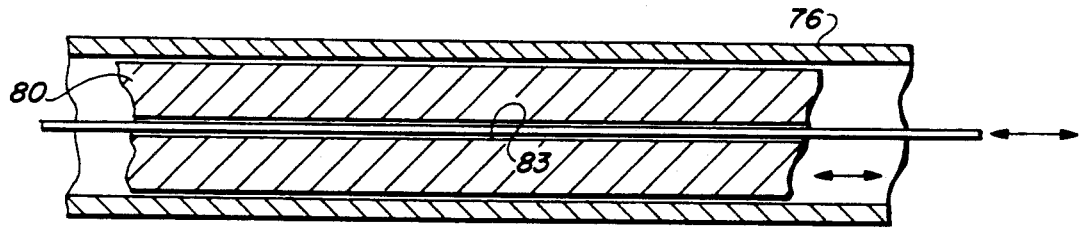

As an alternative form of construction as shown in FIG. 20, the driver section 72 (FIG. 11) simply consists of the thin walled delivery device 76, through which the driver mechanism 80 extends.

Figure 21:
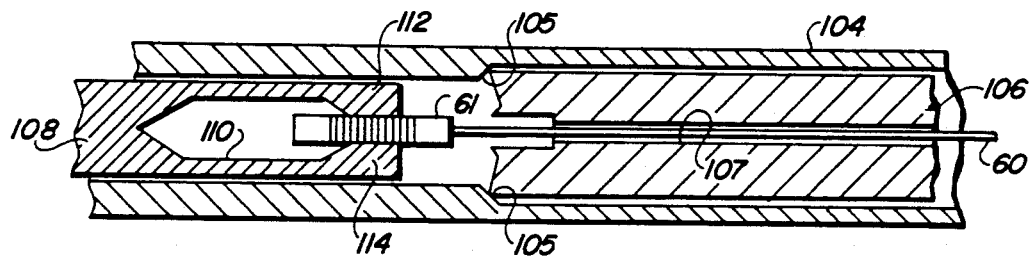
Figure 22:
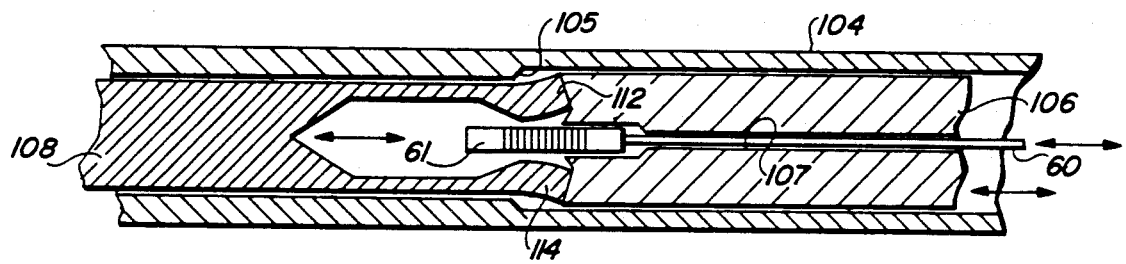

In the arrangement shown in FIGS. 12-15, it was noted that the driver mechanism 80 moves along the guide wire or needle 60, which remains stationary, in order to drive the fastener 42 into the meniscus under treatment. There are, however, certain circumstances and design criteria which require both the driver and the guide wire or needle to both move toward the meniscus; see, for example, the arrangement shown in FIGS. 16 and 17. The arrangement shown in FIGS. 21 and 22 provide for such a "double action" movement. Noting FIG. 21, the delivery device 104 includes an internal shoulder 105 which has a smaller inside diameter than the driver mechanism 106. The driver 106 has a central lumen 107 which receives the guide wire or needle 60. The guide wire or needle 60, in turn, has a hub 61 at its proximal extremity which fits between a pair of jaws 112, 114 of an actuator arm 108. The actuator arm 108 has an opening 110 rearwardly of the jaws 112, 114. The manner in which the "double action" obtains is illustrated in FIG. 22; as the actuator arm extends toward the distal end, the hub 61 is held firmly between the jaws 112, 114, thus pushing the hub and the associated guide wire or needle 60 toward the distal end. As the jaws 112, 114 pass across the shoulder 105, the jaws bias outwardly out of contact with the hub 61 thus disengaging from the hub and discontinuing any further movement of the guidewire or needle 60. However, the jaws 112, 114 then engage the proximal extremity of the driver 106, thereafter pushing the driver toward the distal end so as to force the fastener (i.e. fastener 42 in FIG. 16) out of the distal end.

Three alternate arrangements for the actuator section 70 of the fastener delivery system 64 (FIG. 11) will now be described with reference to FIGS. 23-25.

Figure 23:
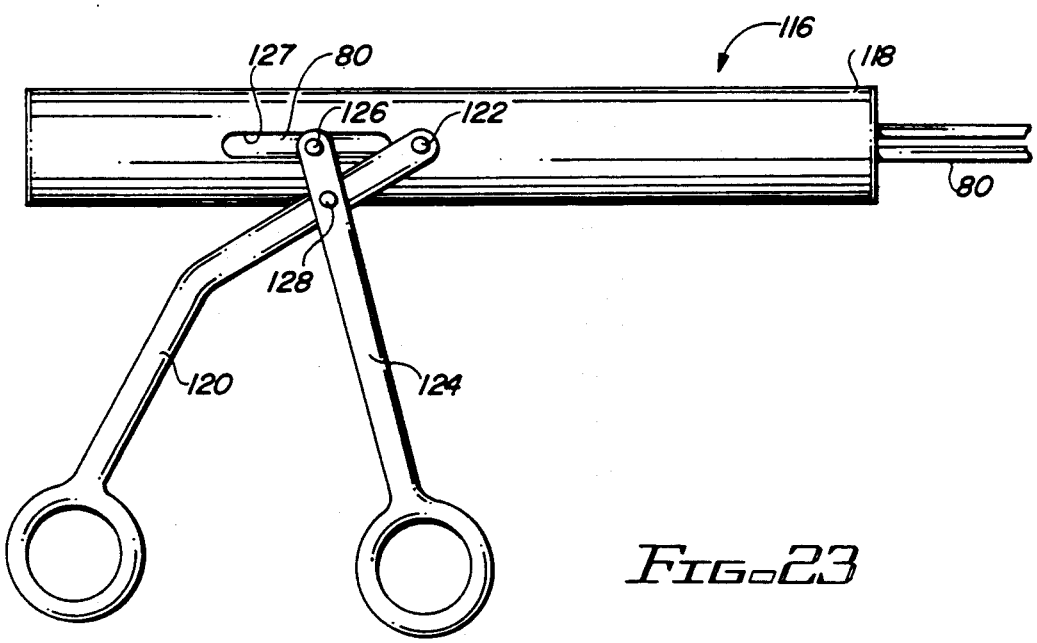
FIGS. 23–25 illustrate alternate forms of the proximal actuator portion of the fastener delivery system.

In FIG. 23, the actuator 116 includes a body member 118 and a pair of scissor arms 120, 124. Scissor arm 120 is pivoted to the body member 118 at pivot 122, and scissor arm 124 is pivoted to arm 120 at pivot 128 and also to the driver at pivot 126 through an aperture 127 in the body 118. It will be understood by those skilled in the art that the moving of the finger grip sections of the pivot arms 120, 124 toward and away from each other extend and retract the driver 80 toward and away from the distal end of the delivery system.

Figure 24:
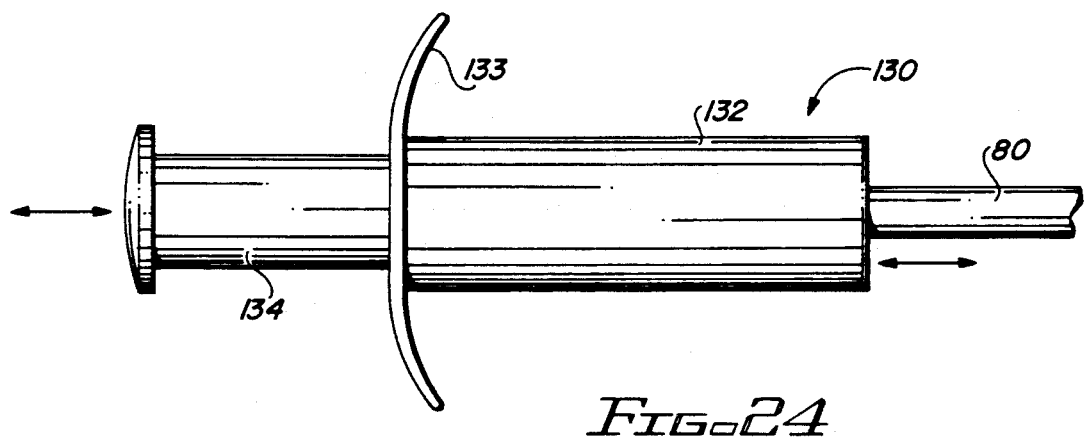
Figure 25:
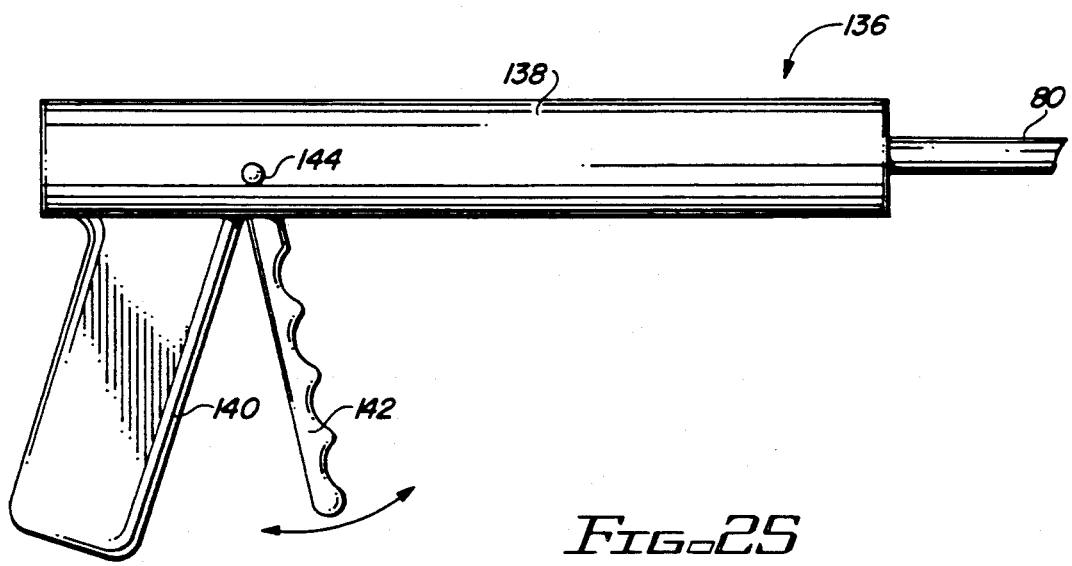

In FIG. 24, the actuator 130 includes a body 132, and a plunger 134 which is in direct mechanical contact with the driver 80. As the plunger 134 extends into the body 132, the driver 80 is operated to deliver the fastener into the meniscus under treatment. Similarly, in FIG. 25, actuator 136 includes a body member 138 and a pistol grip 140 with an associated trigger mechanism 142 pivoted inside the body 138 at 144 to the driver 80. Motion of the trigger mechanism 142 extends the driver in the desired manner to deliver the fastener across the meniscal tear.

FIGS. 26 and 27 illustrate complete assemblies of the fastener delivery system utilizing combinations of the various sections described above, and which utilize the section reference numerals of FIG. 11 (i.e., actuator section 70, driver section 72 and flexible tip 74).

In use, the flexible tip 74 is inserted into the central portion 11 of the patient's knee (note FIG. 1). The flexible tip is then pointed outwardly toward the meniscus, so that the needle or guidewire, upon being inserted in the meniscus, will cross the meniscal tear under treatment and form a channel for the fastener; the fastener is then driven across the needle or guidewire to close the tear, without passing the fastener out of the knee. A fastener such as the specific arrangement shown in FIGS. 6 and 7 with flattened sides may be utilized to avoid condylar abrasion, by driving the fastener 24 across the meniscus with the flat sides 31 (or a similar construction feature) upwardly, so that there is no portion of the fastener extending above the dimension of the periphery of the tubular member 26. In this way, there are no protrusions so as to irritate the adjacent condyl while the patient is recovering after the meniscal tear repair procedure. It will be understood that after a period of time, the bioabsorbable material used for the fastener will eventually dissolve, after the tear has healed.

What is claimed is:

1. A method for repairing a tear in a knee meniscus of a patient, comprising the step of:
    providing a delivery device having a proximal end and a distal end, the distal end dimensioned to extend into the interior of the patient's knee;
    inserting the device into the patient's knee so that the distal end extends centrally into the knee;
    fitting a fastener within the device;
    manipulating the device through a curved radius so that the distal end is directed outwardly toward the tear in the meniscus; and thereafter
    extending and releasing the fastener through the curved radius and out of the distal end of the device outwardly through the meniscus and across the tear to close and bind the tear without passing the fastener out of the meniscus.

2. The method recited in claim 1 wherein the fastener extending step comprises pushing the fastener through the device responsive to an actuating step at the proximal end of the delivery device.

3. The method recited in claim 2 wherein the actuating step comprises extending an actuator through the device.

4. The method recited in either claim 1, 2 or 3 further comprising the step of locking the fastener against inward movement toward the center of the patient's knee.

5. The method recited in either claim 1, 2 or 3 wherein the inserting and manipulating steps comprise first inserting the distal end into the patient's knee, and thereafter manipulating the distal end centrally and against the meniscus under repair.

6. The method recited in claim 1 wherein the fastener is bioabsorbable.

7. The method recited in either claim 1, 2 or 3 further comprising the step of constructing and extending the fastener in a direction through the meniscus under repair so as to avoid condylar abrasion.

8. A method for repairing a tear in a knee meniscus of a patient, comprising the steps of:
    providing a relatively rigid fastener of a nontoxic, bioabsorbable material, the fastener having locking means along its length; and
    inserting the fastener into the patient's knee, manipulating the fastener through a curved radius and then outwardly across the meniscal tear, without extending the fastener through the outer perimeter of the knee.

9. The method recited in claim 8 wherein the inserting step further comprises the step of:
providing a delivery device having a proximal end and a curving distal end dimensioned to extend into the interior of the patient's knee and adapted to receive the fastener; and
inserting the curving distal end into the patient's knee.

10. The method recited in claim 8 further comprising the step of constructing and extending the fastener in a direction through the meniscus under repair so as to avoid condylar abrasion.

11. A method for repairing a tear in a knee meniscus of a patient without sutures, comprising the steps of:

providing a delivery device having a proximal end and a distal end, the distal end configured to extend first into the interior of a patient's knee, through a curved radius and then outwardly toward the meniscus under repair;
providing a non-toxic, bioabsorbable fastener having locking means;
fitting the fastener within the device;
inserting the distal end of the device through the curved radius and into the central portion of the patient's knee;
manipulating the device so as to direct the distal end toward the meniscal tear under treatment; and thereafter
driving the fastener through the curved radius and out of the distal end of the device, through the meniscus and across the tear under treatment.

* * * * *